US009770281B2

(12) United States Patent
Rencher et al.

(10) Patent No.: US 9,770,281 B2
(45) Date of Patent: *Sep. 26, 2017

(54) ELECTROSURGICAL APPARATUS WITH RETRACTABLE BLADE

(71) Applicant: Bovie Medical Corporation, Clearwater, FL (US)

(72) Inventors: Jeffrey C. Rencher, Sarasota, FL (US); Gregory A. Konesky, Hampton Bays, NY (US); Borislav S. Simeonov, St. Petersburg, FL (US)

(73) Assignee: Bovie Medical Corporation, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,917

(22) Filed: Jun. 22, 2015

(65) Prior Publication Data

US 2015/0366602 A1 Dec. 24, 2015

Related U.S. Application Data

(63) Continuation of application No. 13/289,060, filed on Nov. 4, 2011, now Pat. No. 9,060,765.

(Continued)

(51) Int. Cl.
*A61B 18/04* (2006.01)
*A61B 18/14* (2006.01)
*A61B 18/00* (2006.01)

(52) U.S. Cl.
CPC ........ *A61B 18/042* (2013.01); *A61B 18/1402* (2013.01); *A61B 2018/00601* (2013.01); *A61B 2018/147* (2013.01); *A61B 2018/1475* (2013.01)

(58) Field of Classification Search
CPC .............. A61B 18/042; A61B 18/1402; A61B 2018/00601; A61B 2018/147; A61B 2018/1475

(Continued)

(56) References Cited

U.S. PATENT DOCUMENTS 1,813,902 A 7/1931 Bovie
2,435,442 A 2/1948 Gurewitsch (Continued)

FOREIGN PATENT DOCUMENTS

EP 0878263 11/1998
EP 1764057 3/2007

(Continued)

OTHER PUBLICATIONS

European Search Report for European Application No. 11008861.4; dated Jan. 25, 2015; five (5) pages.

(Continued)

*Primary Examiner* — Carl H Layno
*Assistant Examiner* — Erin M Piateski
(74) *Attorney, Agent, or Firm* — Gerald E. Hespos; Michael J. Porco; Matthew T. Hespos

(57) ABSTRACT

An electrosurgical apparatus with a retractable blade for use in cold plasma applications, electrosurgical cutting and mechanical cutting is provided. The electrosurgical apparatus employs a tip of the retractable blade as a sharp conductive point to generate a plasma beam or discharge. When the blade is retracted within the electrosurgical apparatus, it is electrically energized while an inert gas flows over it, producing a cold plasma discharge. In the de-energized state, the blade is advanced and used as a traditional, mechanical surgical blade.

15 Claims, 7 Drawing Sheets

US 9,770,281 B2

Page 2

Related U.S. Application Data

(60) Provisional application No. 61/411,174, filed on Nov. 8, 2010.

(58) Field of Classification Search
USPC .................................................. 606/45
See application file for complete search history.

(56) References Cited

U.S. PATENT DOCUMENTS

| | | | |
|---|---|---|---|
| 3,239,730 A | 3/1966 | Farago | |
| 3,801,766 A | 4/1974 | Morrison, Jr. | |
| 4,127,110 A | 11/1978 | Bullara | |
| 4,545,375 A | 10/1985 | Cline | |
| 4,580,562 A * | 4/1986 | Goof | A61B 18/12 606/39 |
| 4,619,258 A | 10/1986 | Pool | |
| 4,625,723 A | 12/1986 | Altnether et al. | |
| 4,632,109 A | 12/1986 | Paterson | |
| 4,708,137 A | 11/1987 | Tsukagoshi | |
| 4,827,927 A | 5/1989 | Newton | |
| 5,088,997 A | 2/1992 | Delahuerga et al. | |
| 5,098,430 A | 3/1992 | Fleenor | |
| 5,207,675 A | 5/1993 | Canady | |
| 5,256,138 A * | 10/1993 | Burek | A61B 18/042 606/42 |
| 5,269,780 A | 12/1993 | Roos | |
| 5,306,238 A | 4/1994 | Fleenor | |
| 5,400,267 A | 3/1995 | Denen et al. | |
| 5,425,375 A | 6/1995 | Chin et al. | |
| 5,449,356 A * | 9/1995 | Walbrink | A61B 18/1482 606/37 |
| 5,626,575 A | 5/1997 | Crenner | |
| 5,647,869 A | 7/1997 | Goble et al. | |
| 5,651,780 A | 7/1997 | Jackson et al. | |
| 5,660,657 A | 8/1997 | Rajala et al. | |
| 5,693,042 A | 12/1997 | Boiarski et al. | |
| 5,693,044 A | 12/1997 | Cosmescu | |
| 5,776,092 A | 7/1998 | Farin et al. | |
| 5,800,427 A * | 9/1998 | Zamba | A61B 18/1402 606/39 |
| 6,193,715 B1 | 2/2001 | Wrublewski et al. | |
| 6,225,593 B1 | 5/2001 | Howieson et al. | |
| 6,293,945 B1 | 9/2001 | Parins et al. | |
| 6,325,799 B1 | 12/2001 | Goble | |
| 6,391,027 B1 | 5/2002 | Farin et al. | |
| 6,409,724 B1 | 6/2002 | Penny et al. | |
| 6,458,125 B1 | 10/2002 | Cosmescu | |
| 6,475,215 B1 | 11/2002 | Tanrisever | |
| 6,558,383 B2 | 5/2003 | Cunningham et al. | |
| 6,578,579 B2 | 6/2003 | Burnside et al. | |
| 6,652,514 B2 | 11/2003 | Ellman et al. | |
| 6,740,079 B1 | 5/2004 | Eggers | |
| 6,770,071 B2 | 8/2004 | Woloszko et al. | |
| 6,899,538 B2 | 5/2005 | Matoba | |
| 6,958,063 B1 | 10/2005 | Soll et al. | |
| 6,994,707 B2 | 2/2006 | Ellman et al. | |
| 7,033,353 B2 | 4/2006 | Stoddard et al. | |
| 7,115,121 B2 | 10/2006 | Novak | |
| 7,156,842 B2 | 1/2007 | Sartor et al. | |
| 7,156,844 B2 | 1/2007 | Reschke et al. | |
| 7,169,144 B2 | 1/2007 | Hoey | |
| 7,244,257 B2 | 7/2007 | Podhajsky et al. | |
| 7,316,682 B2 | 1/2008 | Konesky | |
| 7,335,199 B2 | 2/2008 | Goble et al. | |
| 7,443,296 B2 | 10/2008 | Mezhinsky et al. | |
| 7,479,140 B2 | 1/2009 | Ellman et al. | |
| 7,481,809 B2 | 1/2009 | Stern et al. | |
| 7,503,917 B2 | 3/2009 | Sartor et al. | |
| 7,568,619 B2 | 8/2009 | Todd et al. | |
| 7,578,817 B2 | 8/2009 | Canady | |
| 7,654,975 B2 | 2/2010 | Mantell | |
| 7,749,221 B2 | 7/2010 | Rontal | |
| 7,815,638 B2 | 10/2010 | Farin et al. | |
| 8,016,824 B2 | 9/2011 | Buchman, II et al. | |
| 8,022,327 B2 | 9/2011 | Blomeyer | |
| 8,177,782 B2 | 5/2012 | Beller et al. | |
| 8,216,220 B2 | 7/2012 | Jensen et al. | |
| 8,319,134 B2 | 11/2012 | Blomeyer | |
| 8,353,905 B2 | 1/2013 | Jensen et al. | |
| 8,562,598 B2 | 10/2013 | Falkenstein et al. | |
| 8,568,400 B2 | 10/2013 | Gilbert | |
| 8,689,606 B2 | 4/2014 | Schellekens et al. | |
| 2002/0013582 A1 | 1/2002 | Mulier et al. | |
| 2003/0050633 A1 | 3/2003 | Ellman et al. | |
| 2003/0130655 A1 | 7/2003 | Woloszko et al. | |
| 2004/0148903 A1 | 8/2004 | Cash | |
| 2004/0243120 A1 | 12/2004 | Orszulak et al. | |
| 2005/0075630 A1 | 4/2005 | Truckai et al. | |
| 2005/0148903 A1 | 7/2005 | Diamantopoulos | |
| 2006/0122595 A1 * | 6/2006 | Farin | A61B 18/042 606/45 |
| 2007/0028669 A1 | 2/2007 | Brewster | |
| 2007/0049926 A1 | 3/2007 | Sartor | |
| 2007/0083247 A1 | 4/2007 | Wyeth et al. | |
| 2007/0093810 A1 | 4/2007 | Sartor et al. | |
| 2007/0135812 A1 | 6/2007 | Sartor | |
| 2007/0158209 A1 | 7/2007 | Kang et al. | |
| 2007/0260239 A1 | 11/2007 | Podhajsky et al. | |
| 2008/0071261 A1 | 3/2008 | Orszulak | |
| 2008/0108985 A1 | 5/2008 | Konesky | |
| 2008/0140066 A1 | 6/2008 | Davison et al. | |
| 2009/0005772 A1 | 1/2009 | Penny | |
| 2009/0125023 A1 | 5/2009 | Stephen et al. | |
| 2009/0143778 A1 | 6/2009 | Sartor et al. | |
| 2009/0149851 A1 | 6/2009 | Craig | |
| 2009/0248022 A1 * | 10/2009 | Falkenstein | A61B 18/1442 606/51 |
| 2010/0094288 A1 | 4/2010 | Kerr | |
| 2010/0262139 A1 | 10/2010 | Beller et al. | |
| 2011/0238053 A1 | 9/2011 | Brannan et al. | |
| 2012/0116397 A1 | 5/2012 | Rencher et al. | |
| 2012/0123405 A1 | 5/2012 | Moua et al. | |
| 2012/0232540 A1 | 9/2012 | Baur et al. | |
| 2012/0330305 A1 | 12/2012 | Zoran et al. | |
| 2012/0330307 A1 | 12/2012 | Ladtkow et al. | |
| 2013/0046290 A1 | 2/2013 | Palmer et al. | |
| 2013/0237982 A1 | 9/2013 | Rencher et al. | |
| 2013/0296846 A1 | 11/2013 | Canady et al. | |
| 2014/0005665 A1 | 1/2014 | Konesky et al. | |
| 2014/0018795 A1 | 1/2014 | Shilev et al. | |

FOREIGN PATENT DOCUMENTS

| | | |
|---|---|---|
| EP | 2263728 | 12/2010 |
| EP | 2449992 | 5/2012 |
| WO | 2004096315 | 11/2004 |

OTHER PUBLICATIONS

European Search Report for European Application No. 15000707.8; dated May 28, 2015; four (4) pages.

* cited by examiner

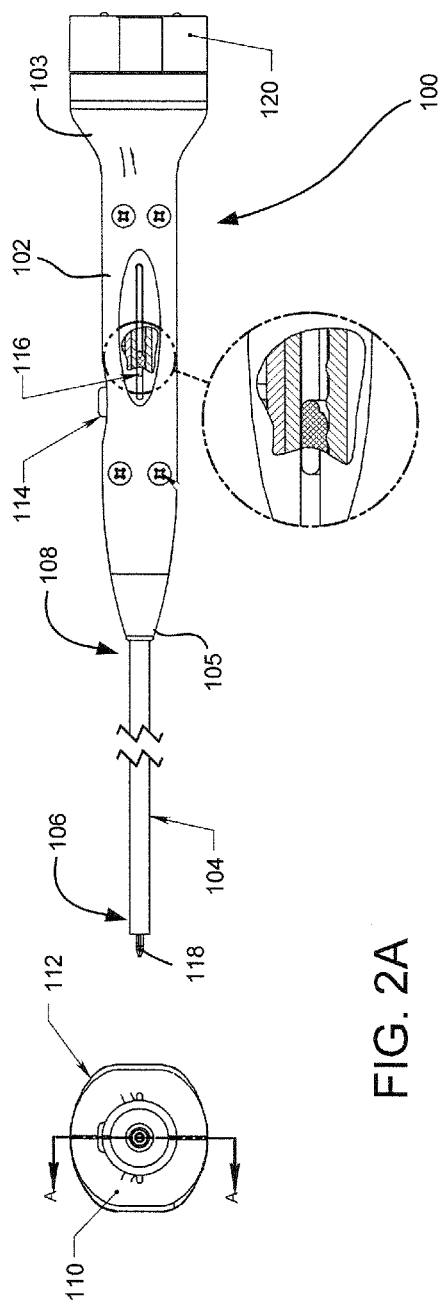
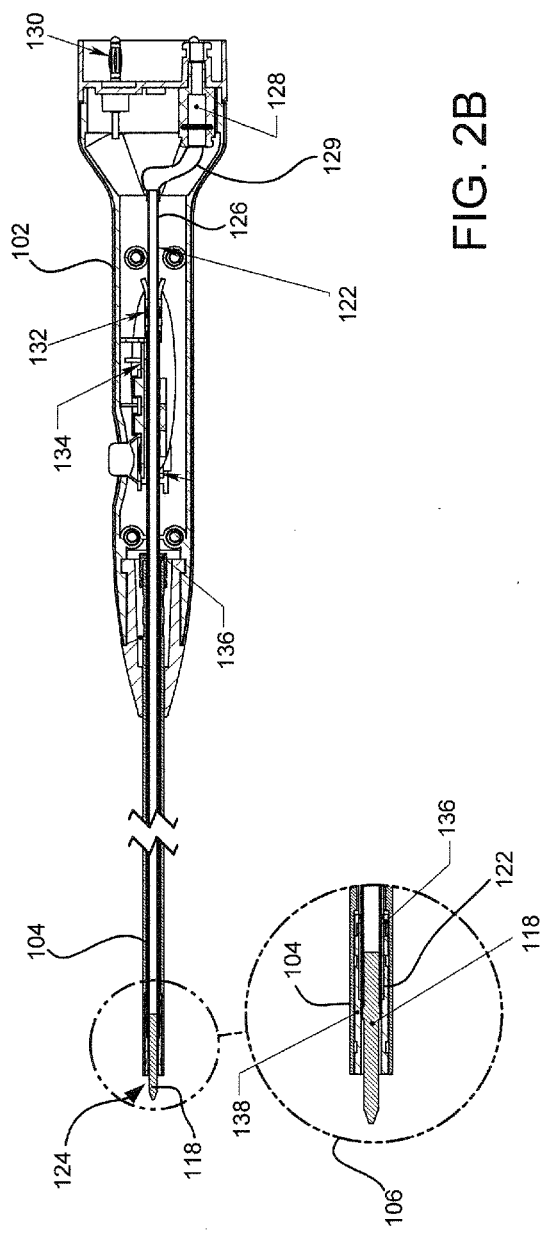
FIG. 2A
FIG. 2B

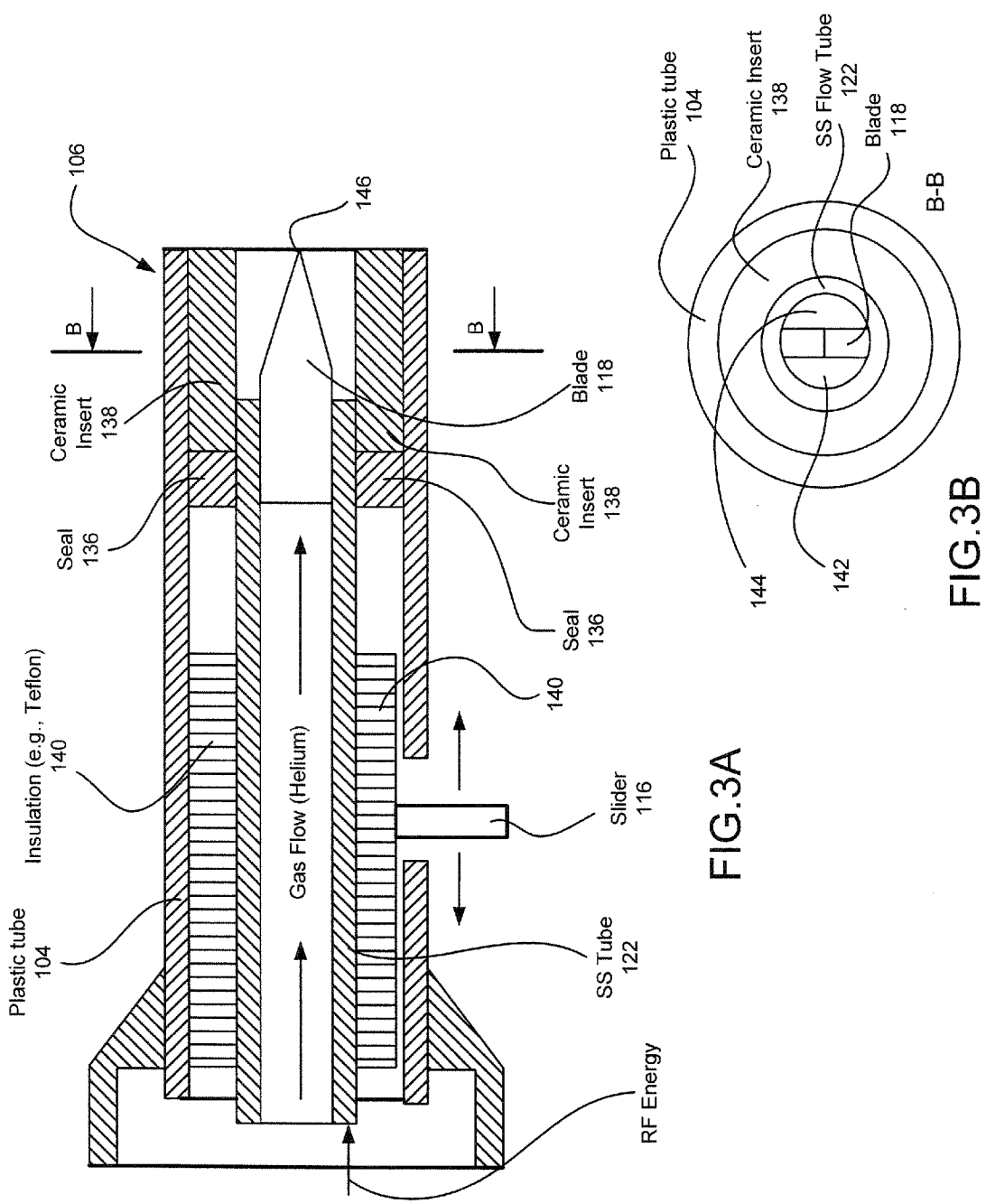

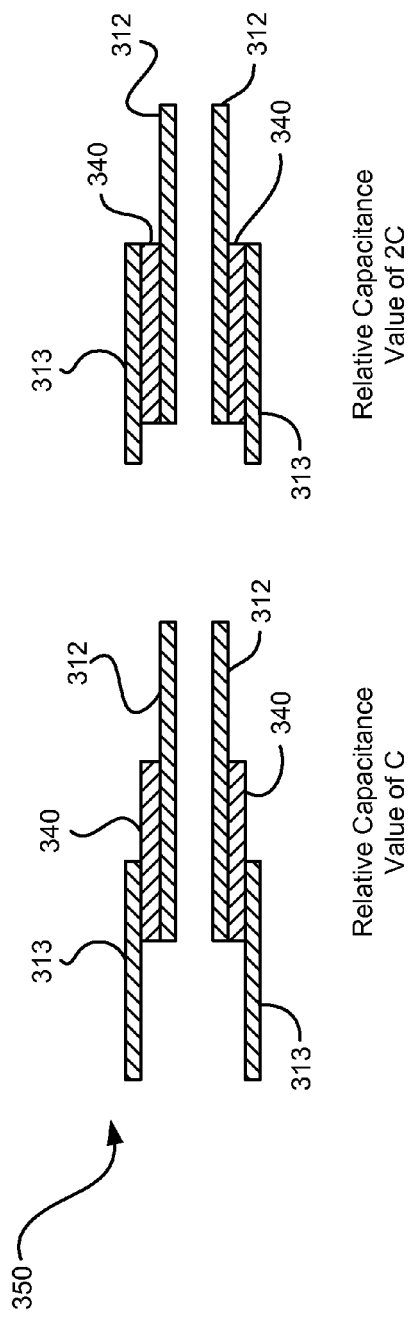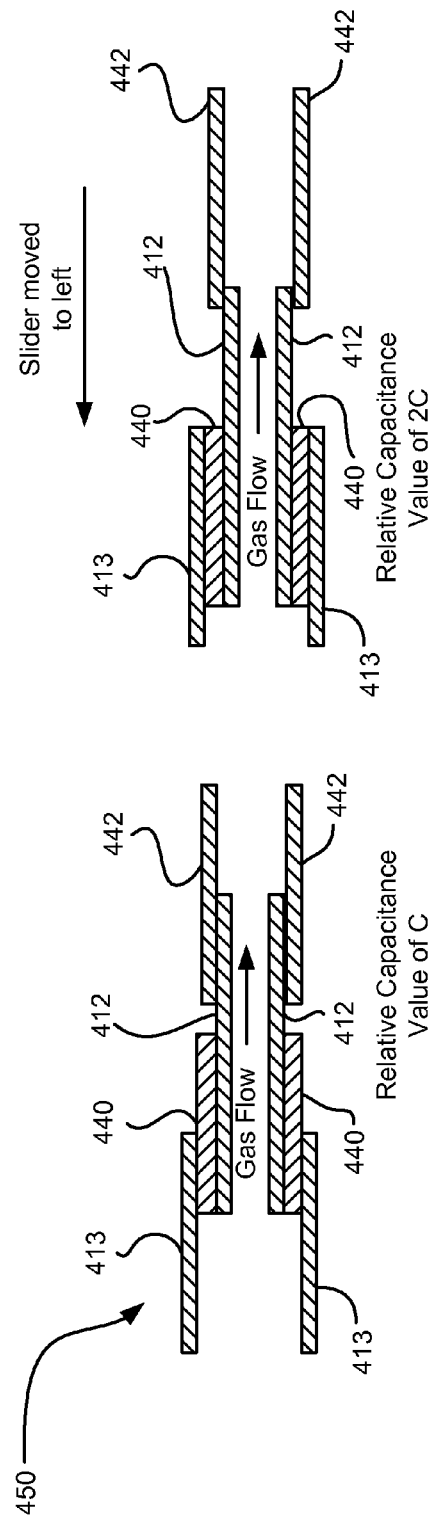

ELECTROSURGICAL APPARATUS WITH RETRACTABLE BLADE

PRIORITY

This application is a continuation application of U.S. application Ser. No. 13/289,060, filed Nov. 4, 2011, now U.S. Pat. No. 9,060,765, which claims priority on U.S. Provisional Patent Appl. No. 61/411,174, filed Nov. 8, 2010, entitled "ELECTROSURGICAL APPARATUS WITH RETRACTABLE BLADE", the content of which is hereby incorporated by reference in its entirety.

BACKGROUND

Field

The present disclosure relates generally to electrosurgery and electrosurgical systems and apparatuses, and more particularly, to an electrosurgical apparatus with a retractable blade for use in cold plasma applications, electrosurgical cutting and mechanical cutting.

Description of the Related Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. In the latter example, the process can be relatively slow, generate large volumes of noxious smoke with vaporized and charred tissue, and may cause collateral damage to surrounding healthy tissue when high power electrosurgical energy is used. Precision accuracy can also be a problem, due to the width of the plasma beam.

Often, a simple surgical knife is used to excise the tissue in question, followed by the use of a cold plasma applicator for cauterization, sterilization, and hemostasis. An improved approach would have both facilities in the same surgical tool.

SUMMARY

The present disclosure relates to an electrosurgical apparatus with a retractable blade for use in cold plasma applications, electrosurgical cutting and mechanical cutting. The advancement of this new approach is to use the tip of the retractable blade as the sharp conductive point to generate the plasma beam or discharge. When the blade is retracted within the electrosurgical apparatus, it is electrically energized while an inert gas flows over it, producing a cold plasma discharge. In the de-energized state, the blade is advanced and used as a traditional surgical blade. In a third state, the blade is advanced and used while both electrically energized and with inert gas flow. This third state resembles an electrosurgical knife approach, however, with the addition of the inert gas flow, cuts made show virtually no eschar, with very little collateral damage along the side walls of the cut. Furthermore, the cutting speed is considerably faster, with less mechanical cutting resistance as compared to when the knife blade is not electrically energized. Hemostasis is also affected during this process.

In one aspect of the present disclosure, an electrosurgical apparatus is provided including a housing having a passage extending therethrough, the housing having a proximal end and a distal end; an electrically conducting tube having a proximal end and a distal end, the electrically conducting tube being disposed in the passage of the housing; an insulating outer tube having a proximal end and a distal end, the outer tube disposed around the electrically conducting tube with the proximal end of the outer tube coupled to the distal end of the housing, the electrically conducting tube being movable along a longitudinal axis of the housing and outer tube; and an electrically conducting blade coupled to the distal end of the electrically conducting tube, wherein in a first position of the electrically conducting tube, the blade extends beyond the distal end of the outer tube for mechanical cutting and, in a second position of the electrically conducting tube, the blade is retracted within the outer tube and is energized via the electrically conducting tube to form plasma when an inert gas flows through the electrically conducting tube, wherein the electrically conducting tube is configured as a structural current limiting capacitor to limit current applied to a operative site when the electrically conducting tube is energized.

In another aspect, the electrically conducting tube includes a first, inner flow tube having a proximal end and a distal end; a second, outer flow tube having a proximal end and a distal end; and a cylindrical insulator disposed around the distal end of the first, inner flow tube for coupling the first, inner flow tube to an inner portion of the proximal end of the second, outer flow tube, wherein an overlapping portion of the first, inner flow tube, the cylindrical insulator and the second, outer flow tube forms the structural current limiting capacitor.

In a further aspect, at least one of the first, inner flow tube and second, outer flow tube is movable relative to each other to varying a capacitance value of the structural current limiting capacitor.

In another aspect, the electrosurgical apparatus includes a first slider member coupled to the first, inner flow tube for variably setting a current limit of the capacitor, the first slider member being accessible on the housing.

In yet another aspect, the electrosurgical apparatus includes a second slider member coupled to the second, outer flow tube for extending and retracting the blade, the second slider member being accessible on the housing.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a schematic diagram of an electrosurgical apparatus in accordance with an embodiment of the present disclosure;

FIG. 2B is a cross sectional view of the electrosurgical apparatus shown in FIG. 2A taken along line A-A;

FIG. 3A is an enlarged cross sectional view of the electrosurgical apparatus in accordance with an embodiment of the present disclosure;

FIG. 3B illustrates a front view of the electrosurgical apparatus shown in FIG. 3A taken along line B-B;

FIGS. 6A and 6B illustrate a variable structural capacitor to be employed in an electrosurgical apparatus in accordance with an embodiment of the present disclosure;

FIGS. 7A and 7B illustrate a variable structural capacitor to be employed in an electrosurgical apparatus in accordance with another embodiment of the present disclosure.

Figure 1:
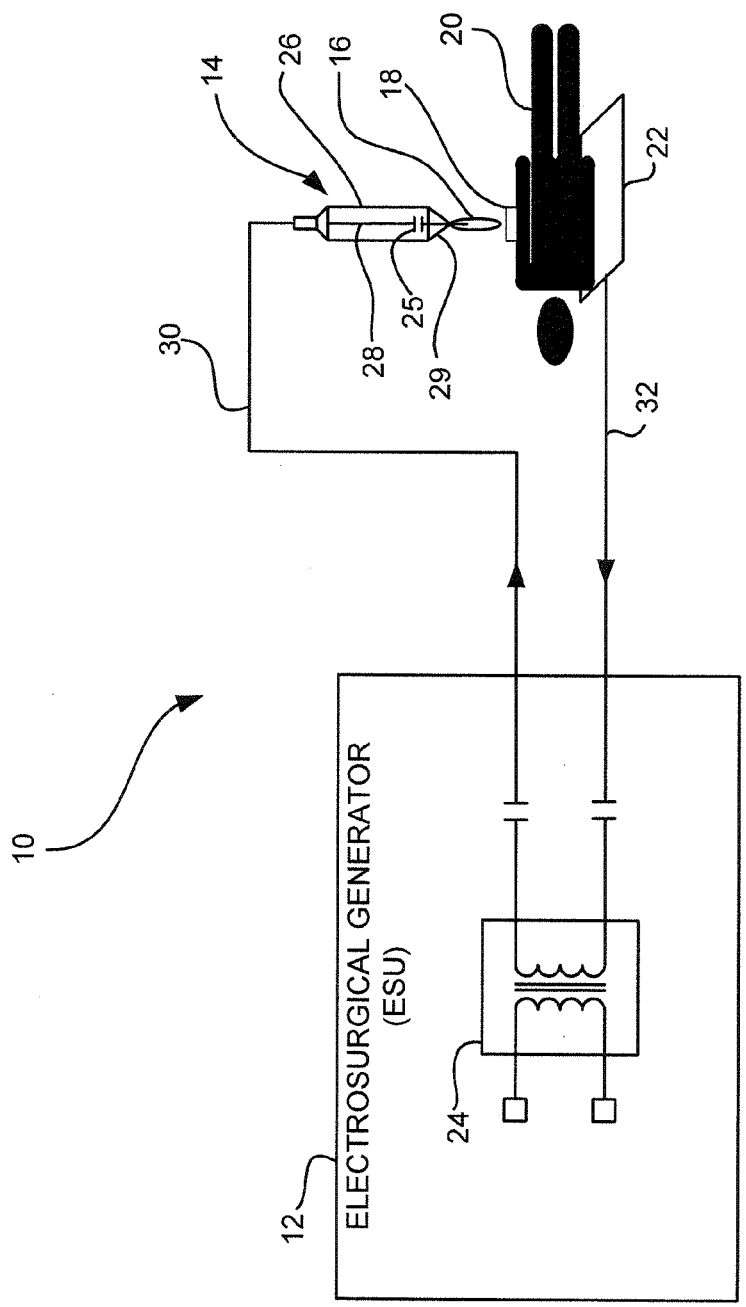
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

FIG. 1 shows an exemplary monopolar electrosurgical system generally indicated as 10 comprising an electrosurgical generator (ESU) generally indicated as 12 to generate power for the electrosurgical apparatus 10 and a plasma generator generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the plasma generator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The plasma generator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivery to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the plasma generator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the plasma generator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Referring to FIG. 2A, an electrosurgical apparatus 100 in accordance with the present disclosure is illustrated. Generally, the apparatus 100 includes a housing 102 having a proximal end 103 and a distal end 105 and a tube 104 having an open distal end 106 and a proximal end 108 coupled to the distal end 105 of the housing 102. The housing 102 includes a right side housing 110 and left side housing 112, and further includes provisions for a button 114 and slider 116. Activation of the slider 116 will expose a blade 118 at the open distal end 106 of the tube 104. Activation of the button 114 will apply electrosurgical energy to the blade 118 and, in certain embodiments, enable gas flow through the flow tube 122, as will be described in detail below.

Additionally, a transformer 120 is provided on the proximal end 103 of the housing for coupling a source of radio frequency (RF) energy to the apparatus 100. By providing the transformer 120 in the apparatus 100 (as opposed to locating the transformer in the electrosurgical generator), power for the apparatus 100 develops from higher voltage and lower current than that required when the transformer is located remotely in the generator, which results in lower thermalization effects. In contrast, a transformer back in the generator produces applicator power at a lower voltage, higher current with greater thermalization effects. Therefore, by providing the transformer 120 in apparatus 100, collateral damage to tissue at the operative site is minimized.

A cross section view along line A-A of the apparatus 102 is shown in FIG. 2B. Disposed within the housing 102 and tube 104 is flow tube 122 which runs along the longitudinal axis of the apparatus 100. On a distal end 124 of the flow tube 122, the blade 118 is retained within the flow tube 122. A proximal end 126 of the flow tube 122 is coupled to a source of gas via a tube connector 128 and flexible tubing 129. The proximal end 126 of the flow tube 122 is also coupled to a source of RF energy via plug 130 which couples to transformer 120. The flow tube 122 is made of an electrically conducting material, preferably stainless steel, as to conduct the RF energy to the blade 118 when being employed for plasma applications or electrosurgical cutting as will be described below. The outer tube 104 is constructed from non-conductive material, e.g., Lestran. The slider 116 is coupled to the flow tube 122 via a retaining collar 132. A printed circuit board (PCB) 134 is disposed in the housing 102 and controls the application of the RF energy from the transformer 120 via the button 114.

It is to be appreciated that the slider 116 may be freely moveable in a linear direction or may include a mechanism for incremental movements, e.g., a ratchet movement, to prevent an operator of the apparatus 100 from over extending the blade 118. By employing a mechanism for incremental movements of the blade 118, the operator will have greater control over the length of the exposed blade 118 to avoid damage to tissue at the surgical site.

An enlarged view of the distal end 106 of the outer tube 104 is also illustrated in FIG. 2B. Here, the blade 118 is coupled to the flow tube 122 which is held in place in the outer tube 104 by at least one seal 136. The at least one seal 136 prevents backflow of gas into tube 104 and housing 102. A cylindrical ceramic insert 138 is disposed in the distal end of the outer tube 104 to maintain the blade along the longitudinal axis of the apparatus 100 and provide structural support during mechanical cutting when the blade is exposed beyond the distal end of the outer tube 104.

The operational aspect of the apparatus 100 will now be described in relation to FIGS. 3A and 3B, where FIG. 3A shows an enlarged cross section of the apparatus and FIG. 3B illustrates a front view of the apparatus.

Referring to FIG. 3A, the flow tube 122 is disposed in the outer tube 104 with a cylindrical insulator 140 disposed around the flow tube 122. Slider 116 is coupled to the insulator 140 and is employed to extend and retract the blade 118. At the distal end 106 of the outer tube 104, the annular or ring shaped seal 136 and cylindrical ceramic insert 138 are disposed about the flow tube 122. As can be seen in FIG. 3B, the generally planar blade 118 is coupled to an inner circumference of the cylindrical flow tube 122 such that two gas passageways 142, 144 are formed on both sides of the blade 118. As gas flows from the proximal end 103 of the housing through the flow tube 122, the gas will pass over the blade 118 out the distal end of the outer tube 104.

When the blade is in the retracted position as shown in FIG. 3A, the apparatus 102 is suitable for generating plasma. In the retracted position, RF energy is conducted to a tip 146 of the blade 118 from an electrosurgical generator (not shown) via the flow tube 122. An inert gas, such as helium or argon, is then supplied to the flow tube from either the electrosurgical generator or an external gas source. As the inert gas flows over the sharp point 146 of the blade 118 that is held at a high voltage and high frequency, a cold plasma beam is generated.

Figure 4:
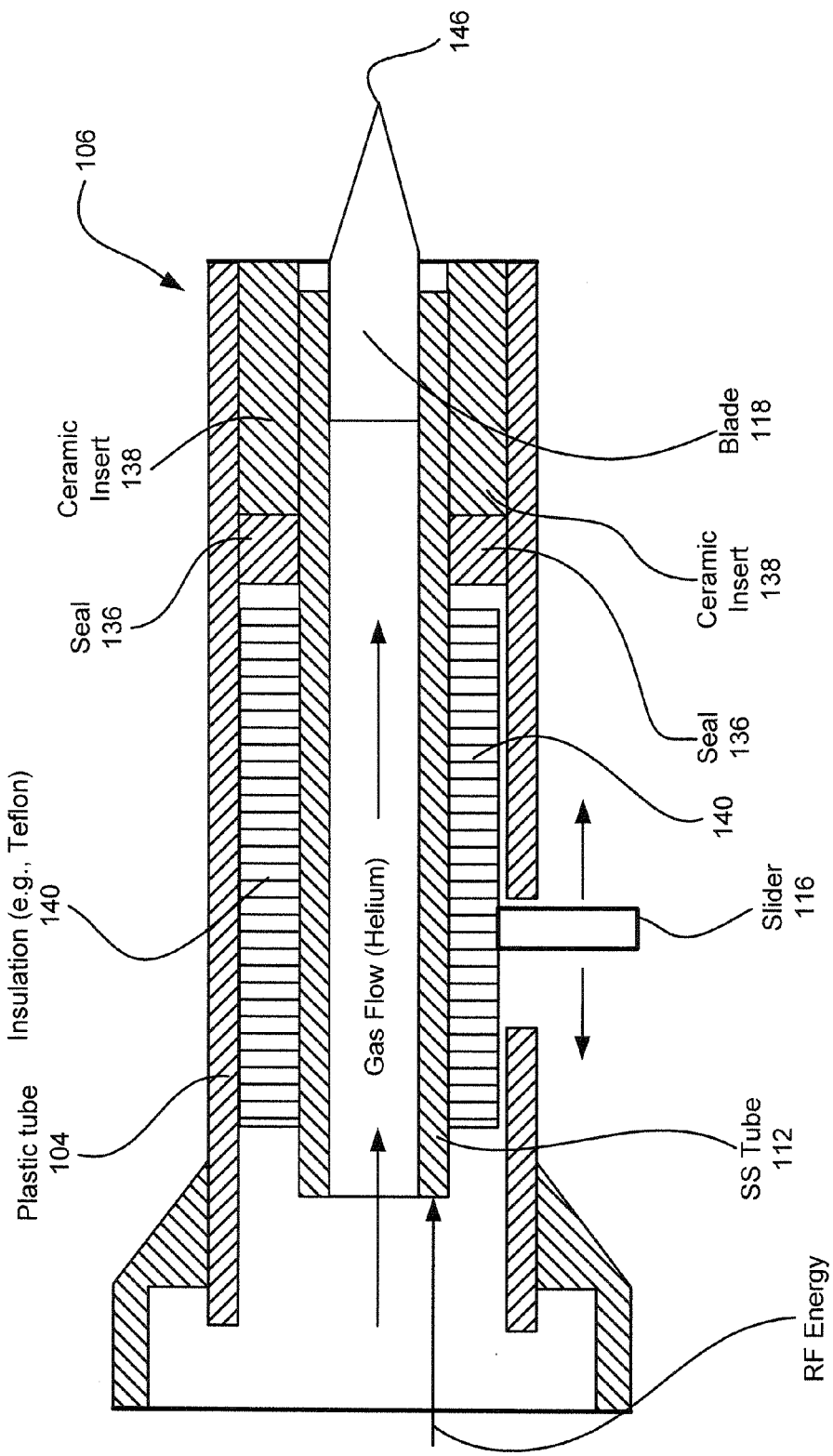
FIG. 4 is an enlarged cross sectional view of the electrosurgical apparatus shown in FIG. 3A with a blade extended.

Referring to FIG. 4, the blade 118 is advanced, via slider 116, so the tip 146 is extended pass the distal end 106 of the outer tube 104. In this state, the blade 118 can be used for two cutting modes: mechanical cutting and electrosurgical cutting. In the mechanical cutting mode, RF or electrosurgical energy is not applied to the flow tube 122 or blade 118, and therefore, the blade 118 is in a de-energized state. In this mode, the blade 118 can be used to excise tissue via mechanical cutting. After the tissue is removed, the blade 118 may be retracted via the slider 116 and electrosurgical energy and gas may be applied via button 114 to generate a cold plasma beam for cauterization, sterilization and/or hemostasis of the operative patient site.

In the electrosurgical cutting mode, the blade 118 is advanced and used while both electrically energized and with inert gas flow. This configuration resembles an electrosurgical knife approach, where the electrosurgical energy does the cutting. However, with the addition of the inert gas flow, cuts made show virtually no eschar, with very little collateral damage along the side walls of the cut. The cutting speed is considerably faster, with less mechanical cutting resistance as compared to when the knife blade is not electrically energized, i.e., the mechanical cutting mode. Hemostasis is also affected during this process.

Figure 5:
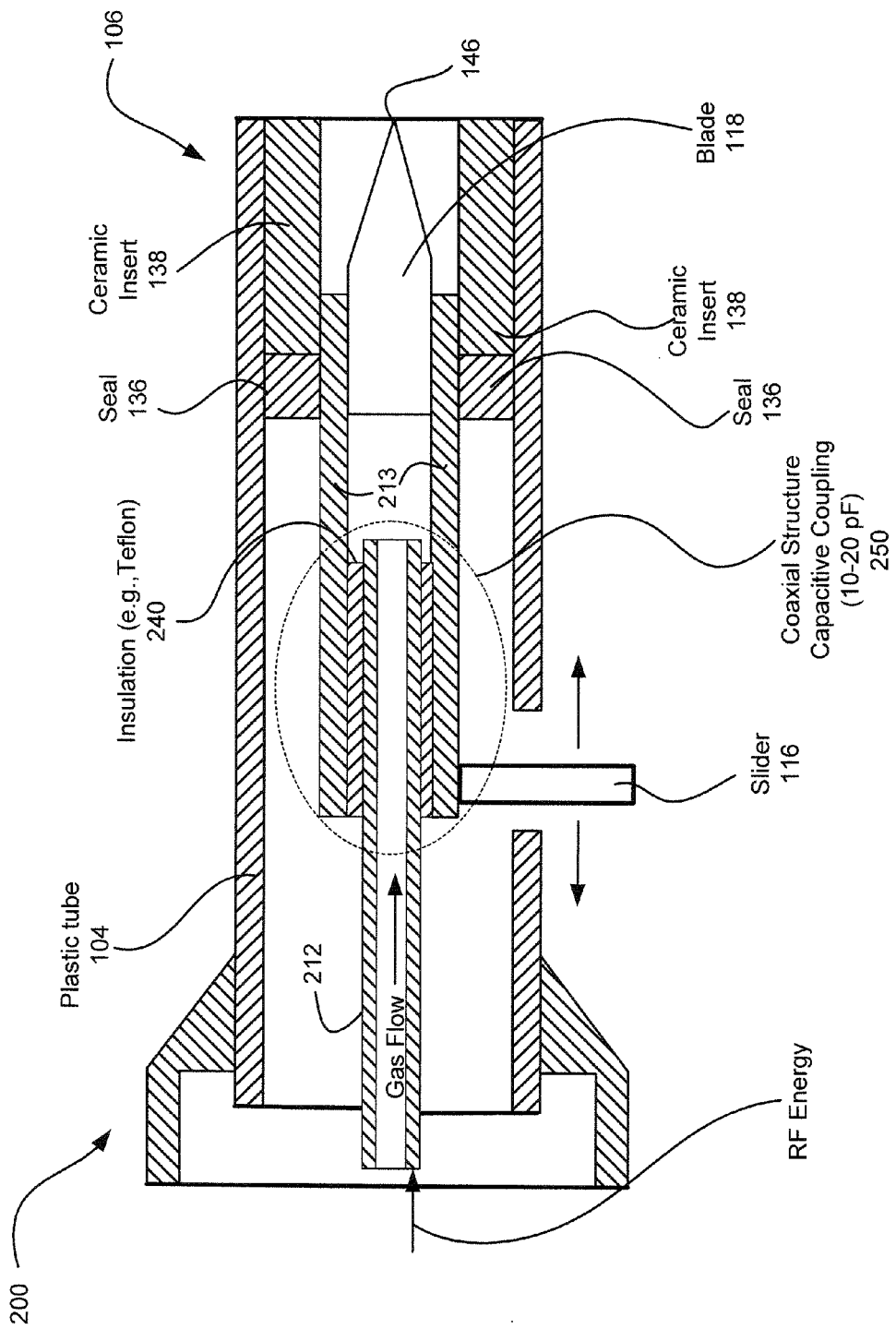
FIG. 5 is a cross sectional view of an electrosurgical apparatus in accordance with another embodiment of the present disclosure.

In another embodiment, an electrosurgical apparatus 200 as shown in FIG. 5 is configured with a structural current limiting capacitor in the distal end of the apparatus or handpiece to limit the current applied to the operative site of the patient. Generally, a capacitor is formed by two parallel conductive plates with an insulating dielectric material in between them. The capacitance is defined by:

$$C = K \epsilon_0 (A/d) \qquad (1)$$

where C is the capacitance in Farads, K is the dielectric constant (sometimes called "relative permittivity"), $\epsilon_0$ is the permittivity of free space (approximately $8.854 \times 10^{-12}$ Farad/meter), A is the area of the capacitor plates, and d is their separation distance. Some typical values for dielectric constant are 1.000 for a vacuum (by definition), 1.00054 for air, 3.8 for fused quartz, and 2.1 for polytetrafluoroethylene ("Teflon"). The parallel plates of a capacitor can take the form of concentric conductive tubes with the insulating dielectric between them as shown in FIG. 5, and can also form a structural, as well as electrical element.

Referring to the embodiment shown in FIG. 5, the flow tube of the apparatus 200 includes a first inner flow tube 212 coupled to a second, outer flow tube 213. The inner flow tube 212 has a smaller outer diameter than the inner diameter of the outer flow tube 213. A cylindrical insulator 240 is disposed around a distal portion of the inner flow tube 212 and then inserted into the outer flow tube 213. As shown in FIG. 5, the inner flow tube 212 is inserted into the outer flow tube 213 approximately a distance equal to the length of the insulator 240. The resulting coaxial structure 250 creates a capacitive coupling for the inner and outer flow tubes 212, 213, where the total capacitance is approximately equal to the capacitance of the coaxial structure 250 plus the capacitance of the remaining length of outer flow tube 213. The coaxial structure 250 acts as a current-limiting capacitor limiting the current applied to the operative site of the patient. When the slider 116 is moved to either extend or retract the blade 118, the components of the coaxial structure 250, including the inner flow tube 212, insulator 240 and outer flow tube 213, move together as a fixed unit. In other aspects, the operation of the embodiment shown in FIG. 5 is similar to the embodiments described above.

In a further embodiment, the electrosurgical apparatus of the present disclosure will include a variable structural capacitor 350 as shown in FIGS. 6A and 6B. The capacitance of a structural capacitor can be varied, assuming a fixed dielectric constant K, by varying the area between the inner and outer conductive tubes. Referring to FIGS. 6A and 6B, inner conductive tube 312 and outer conductive tube 313 are configured to slide relative to each other, with a sleeve of dielectric insulator 340 between them fixed to one of the inner or outer tubes 312, 313 respectively. The degree of overlap of the inner and outer conductive tubes 312, 313 affects the resulting capacitance. In the example shown in FIG. 6A, the insulating dielectric sleeve 340 is fixed to the inner conductive tube 312. The approximately 50% overlap of the outer tube 313 over insulator 340, shown in FIG. 6A, results in a relative capacitance value of "C" and 100% overlap shown in FIG. 6B, in a capacitance of "2C."

While capacitors will block direct current, and provide protection from galvanic currents in an electrosurgical application, capacitors will pass alternating currents as a result of their capacitive reactance, which is defined by:

$$X_C = 1/(2\pi f C) \quad (2)$$

where $X_C$ is the capacitive reactance (in units of resistance), C is the capacitance, and f is the frequency. Due to this inverse relationship, as the capacitance increases, the capacitive reactance decreases. For a given applied voltage and fixed frequency, as the capacitance increases, the amount of current limited by this capacitor will also increase as a result of decreased capacitive reactance.

In the example shown in FIGS. 6A and 6B, the capacitance setting in FIG. 6A limits the current to a lower value than the setting shown in FIG. 6B. In this embodiment, a second slider (not shown) provides the opportunity to adjust this value at the hand piece during a surgical procedure, without being interrupted to make an adjustment at the generator.

It is important to note that when adjusting the current limiting value through varying the relative positions of the inner and outer conductive tubes, that other moveable components, such as the position of the retractable blade, not also be affected. One way to achieve this is with a dual slider configuration 450 as shown in FIGS. 7A and 7B. One side of the slider, or inner conductive tube 412, has the dielectric insulating sleeve 440 to act as the adjustable current limiting capacitor. The other side simply maintains electrical contact to a second outer conductive tube 442 which attaches to the retractable blade (not shown), and allows relative movement without disturbing the position of the retractable blade. This is illustrated in FIGS. 7A and 7B, showing a low current limit value on the left (FIG. 7A), and a high current limit value on the right (FIG. 7B). The position of the inner "slider" tube 412 may be controlled manually by the surgeon via a first slider member, or automatically by electromechanical, pneumatic or similar means. This provides the opportunity to create a feedback loop where the current limit is self-adjusted based on a measured parameter such as absorbed power, tissue temperature, tissue impedance or tissue type. A second slider member may be provided and coupled to the outer tube 442 to extend and retract the blade, when the blade is coupled to the distal end of the outer tube 442.

Figure 8:
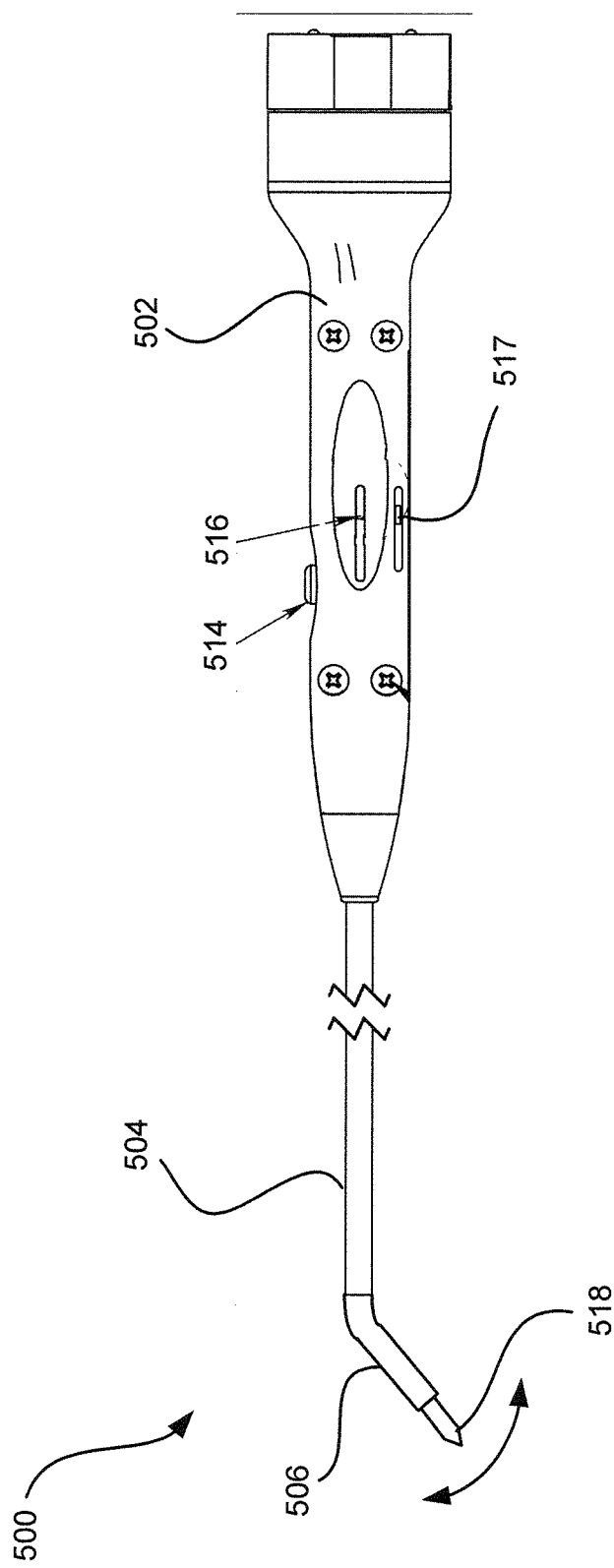
FIG. 8 illustrates an exemplary electrosurgical apparatus including an articulating distal end in accordance with an embodiment of the present disclosure.

In a further embodiment, the electrosurgical apparatus of the present disclosure will have an articulating distal end. Referring to FIG. 8, the electrosurgical apparatus 500 will have similar aspects to the embodiments described above with the distal end 506, e.g., approximately 2 inches, being flexible to maneuver the distal end 506 at the surgical site. An additional control 517, e.g., a slider, trigger, or the like, is provided in the proximal housing 502 to control the bending of the distal end 506. As in the above described embodiments, a button 514 is provided to apply electrosurgical energy to the blade 518 and, in certain embodiment, enable gas flow through the flow tube. Furthermore, slider 516 will expose the blade 518 at the open distal end 506 upon activation.

In one embodiment, the articulating control 517 will include two wires, one pulling to articulate and one pulling to straighten the distal end 506. The outer tube 504 will be the similar to the design shown in FIG. 2 and will be rigid, preferably made of Ultem™ or similar material, up to the last 2 inches which would be made of a material similar to that of a gastrointestinal (GI) flexible scope. In certain embodiments, inside the outer tube 504 is constructed of a mesh infused Teflon™ or similar material and a flexible insulating material that would allow the distal end 506 to bend at least 45° and not collapse the inner tube carrying the gas. The blade 518 will be made of a flexible metallic material such as Nitinol™ that would be able to bend but would retain it's memory in the straightened position. Alternatively, a straight metal blade 518 would be provided with the distal 2 inches made of a linked metal such that it would still carry a current but would be bendable and the cutting portion of the blade 518 would be attached to the distal end of the linked portion.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An electrosurgical apparatus comprising:
    a housing having a passage extending therethrough, the housing having a proximal end and a distal end;
    an electrically conducting tube having a proximal end and a distal end, the electrically conducting tube being disposed in the passage of the housing;
    an insulating outer tube having a proximal end and a distal end, the outer tube disposed around the electrically conducting tube with the proximal end of the outer tube fixed to the distal end of the housing, such that, the outer tube is immoveable with respect to the housing and the electrically conducting tube is movable within the housing and the outer tube along a longitudinal axis of the housing and outer tube; and
    an electrically conducting blade connected to an inner circumference of the distal end of the electrically conducting tube, wherein in a first position of the electrically conducting tube, the electrically conducting blade extends beyond the distal end of the outer tube for mechanical cutting and, in a second position of the electrically conducting tube, the electrically conducting blade is retracted within the outer tube and is energized via the electrically conducting tube to form plasma when an inert gas flows through the electrically conducting tube.

2. The electrosurgical apparatus of claim 1, further comprising a slider member coupled to the electrically conducting tube adjacent to a proximal end thereof and extending through an aperture in the housing, wherein the sliding member is configured for moving the electrically conducting tube within the housing and insulating outer tube thereby extending and retracting the electrically conducting blade in relation to the distal end of the insulating outer tube.

3. The electrosurgical apparatus of claim 2, wherein the slider member includes a ratchet mechanism for incrementally moving the electrically conducting blade.

4. The electrosurgical apparatus of claim 1, further comprising a transformer disposed on the proximal end of the housing, the transformer coupled to the electrically conducting tube for providing electrosurgical energy thereto.

5. The electrosurgical apparatus of claim 4, further comprising a button disposed on the housing and coupled to an output of the transformer for activating and deactivating the electrosurgical energy to the electrically conducting tube.

6. The electrosurgical apparatus of claim 1, wherein the electrically conducting blade is generally planar.

7. The electrosurgical apparatus of claim 6, wherein the electrically conducting blade is connected to the inner circumference of the distal end of the electrically conducting tube, such that, gas passageways are formed on either side of the electrically conducting blade.

8. The electrosurgical apparatus of claim 1, wherein the electrically conducting blade is tapered to a point at a distal end of the electrically conducting blade.

9. The electrosurgical apparatus of claim 1, wherein the electrically conducting tube is configured as a structural current limiting capacitor to limit current applied to an operative site when the electrically conducting tube is energized.

10. An electrosurgical apparatus comprising:
    a housing having a passage extending therethrough, the housing having a proximal end and a distal end;
    an electrically conducting tube having a proximal end and a distal end, the electrically conducting tube being disposed in the passage of the housing;
    an insulating outer tube having a proximal end and a distal end, the outer tube disposed around the electrically conducting tube with the proximal end of the outer tube fixed to the distal end of the housing, such that, the outer tube is immoveable with respect to the housing and the electrically conducting tube is movable within the housing and the outer tube along a longitudinal axis of the housing and outer tube; and
    an electrode connected to an inner circumference of the distal end of the electrically conducting tube, wherein in a first position of the electrically conducting tube, a tip of the electrode extends beyond the distal end of the outer tube for electrosurgical cutting when the tip is energized via the electrically conducting tube and, in a second position of the electrically conducting tube, the tip of the electrode is retracted within the outer tube and is energized via the electrically conducting tube to form plasma when an inert gas flows through the electrically conducting tube.

11. The electrosurgical apparatus of claim 10, further comprising a slider member coupled to the electrically conducting tube adjacent to a proximal end thereof and extending through an aperture in the housing, wherein the sliding member is configured for moving the electrically conducting tube within the housing and insulating outer tube thereby extending and retracting the electrode in relation to the distal end of the insulating outer tube.

12. The electrosurgical apparatus of claim 11, wherein the slider member includes a ratchet mechanism for incrementally moving the electrode.

13. The electrosurgical apparatus of claim 10, wherein the electrically conducting tube is configured as a structural current limiting capacitor to limit current applied to an operative site when the electrically conducting tube is energized.

14. The electrosurgical apparatus of claim 10, further comprising a transformer disposed on the proximal end of the housing, the transformer coupled to the electrically conducting tube for providing electrosurgical energy thereto.

15. The electrosurgical apparatus of claim 14, further comprising a button disposed on the housing and coupled to an output of the transformer for activating and deactivating the electrosurgical energy to the electrically conducting tube.

* * * * *